(12) United States Patent  
Schmälzle et al.

(10) Patent No.: US 8,956,158 B2
(45) Date of Patent: Feb. 17, 2015

(54) SURGICAL TEMPLATE FOR PERFORMING DENTAL IMPLANTOLOGY

(71) Applicant: Swissmeda AG, Zurich (CH)

(72) Inventors: Stefan Schmälzle, Rifferswil (CH); Jörg Danzberg, Seengen (CH)

(73) Assignee: Swissmeda AG, Zurich (CH)

( * ) Notice: Subject to any disclaimer, the term of this patent is extended or adjusted under 35 U.S.C. 154(b) by 0 days.

(21) Appl. No.: 13/731,589

(22) Filed: Dec. 31, 2012

(65) Prior Publication Data

US 2013/0216974 A1 Aug. 22, 2013

(30) Foreign Application Priority Data

Dec. 29, 2011 (EP) .................................... 11196055

(51) Int. Cl.
*A61C 1/08* (2006.01)
*A61C 8/00* (2006.01)
(52) U.S. Cl.
CPC .................. *A61C 8/009* (2013.01); *A61C 1/082* (2013.01); *A61C 1/084* (2013.01)
USPC .......................................................... 433/76
(58) Field of Classification Search
USPC ................................................ 433/72, 75, 76
See application file for complete search history.

(56) References Cited

U.S. PATENT DOCUMENTS

| 1,407,840 | A | * | 2/1922 | Cruttenden | ...................... | 433/76 |
| 5,133,660 | A | * | 7/1992 | Fenick | ............................. | 433/76 |
| 8,398,396 | B2 | * | 3/2013 | Taormina | ........................ | 433/75 |
| 2003/0064346 | A1 | * | 4/2003 | Wennemann | .................... | 433/76 |
| 2009/0202959 | A1 | * | 8/2009 | Ajlouni et al. | .................. | 433/76 |
| 2010/0255441 | A1 | * | 10/2010 | Taormina | ........................ | 433/75 |
| 2011/0111362 | A1 | * | 5/2011 | Haber | ............................. | 433/72 |
| 2011/0217667 | A1 | * | 9/2011 | Groscurth et al. | .............. | 433/68 |

FOREIGN PATENT DOCUMENTS

WO 2011/143725 A1 11/2011

OTHER PUBLICATIONS

International Preliminary Report on Patentability, dated Jul. 10, 2014, issued by The International Bureau of WIPO, in counterpart Application No. PCT/EP2012/077117.

* cited by examiner

*Primary Examiner* — Ralph Lewis
(74) *Attorney, Agent, or Firm* — Sughrue Mion, PLLC

(57) ABSTRACT

A surgical template (10) comprises at least one a drill guide bore (70) surrounded by a guide bore ring (71) and is adapted to be positioned within the oral cavity of patient. The template (10) comprises an inner rail (20) and an outer rail (30) with an interspace (60) in between. At least three inner and three outer connecting points (81, 82) are provided on the inner and outer rail (20, 30) which are adapted to be positioned on portions of the dental apparatus of the patient in his oral cavity to define the three dimensional position and orientation of the at least one drill guide bore ring (71). The rails (20 and 30) are provided in a predetermined varying distance one from the other allowing accommodation of the inner and outer connecting points (81 and 82) on the rails (20, 30), wherein the template (10) further comprises at least two connecting webs (40) connecting the inner rail (20) and the outer rail (30) in a predetermined distance one from the other.

21 Claims, 9 Drawing Sheets

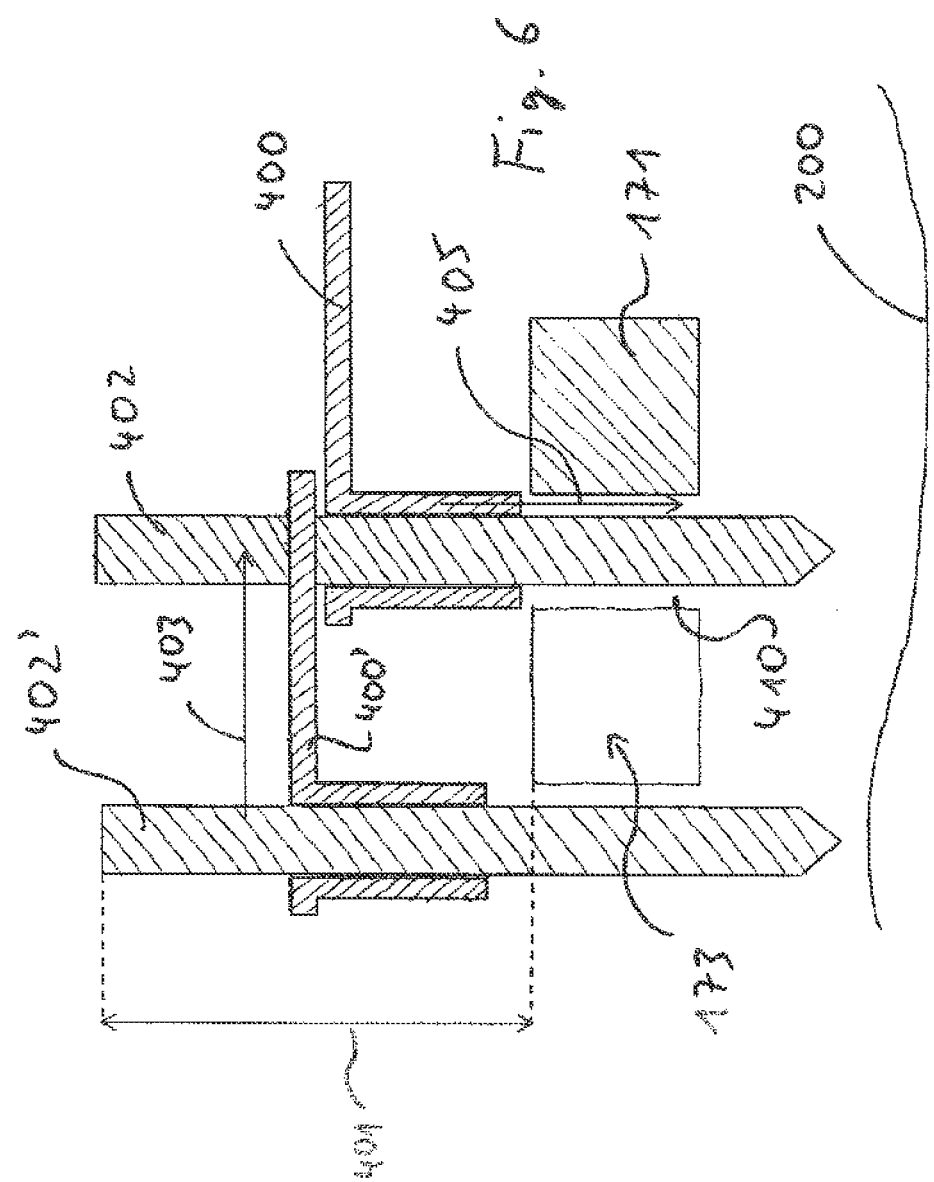

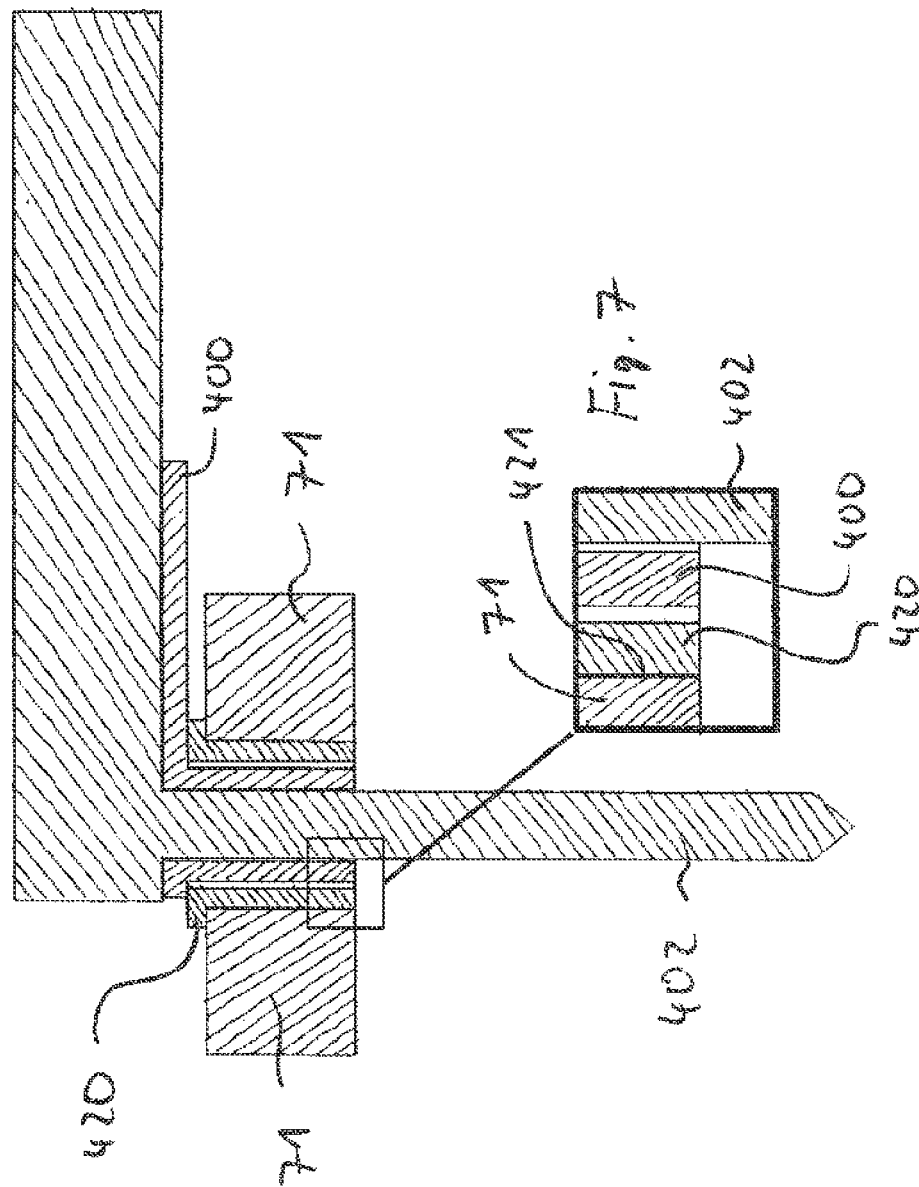

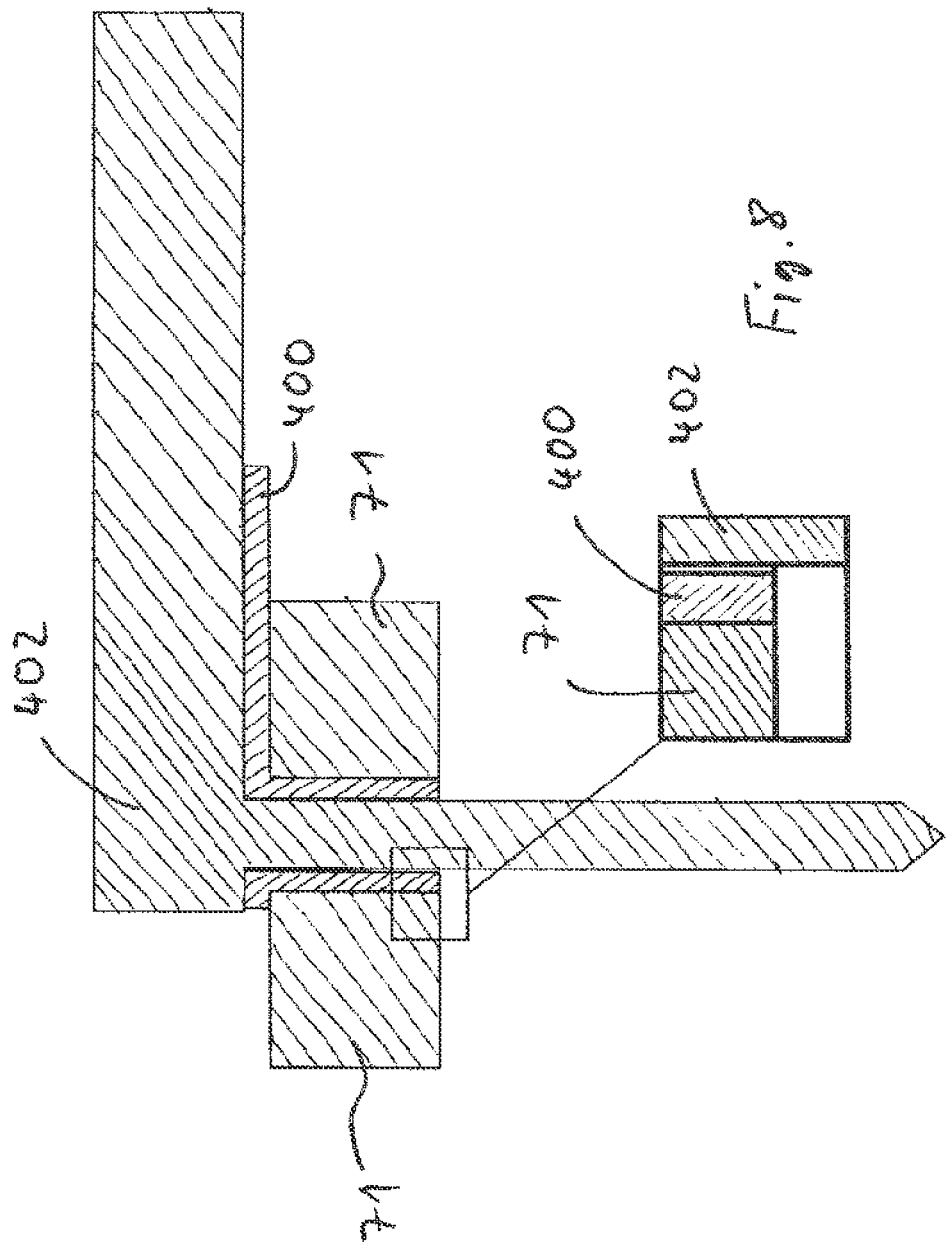

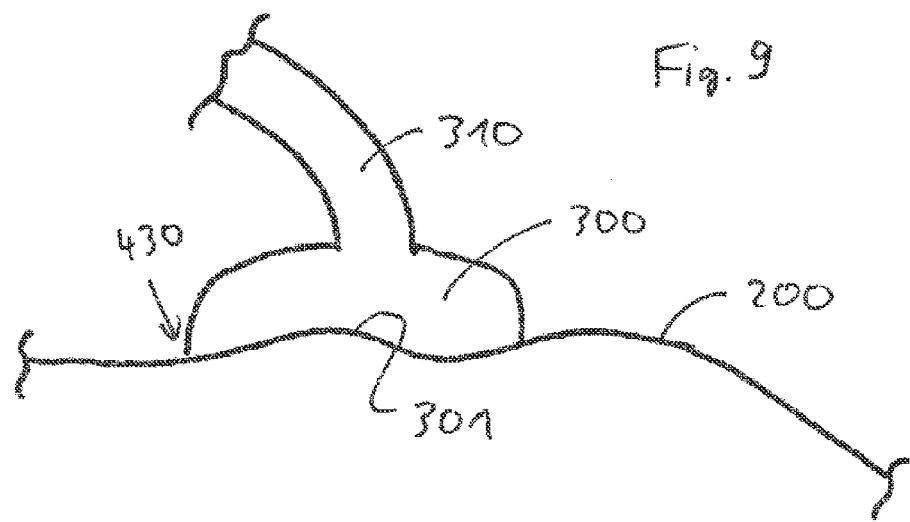
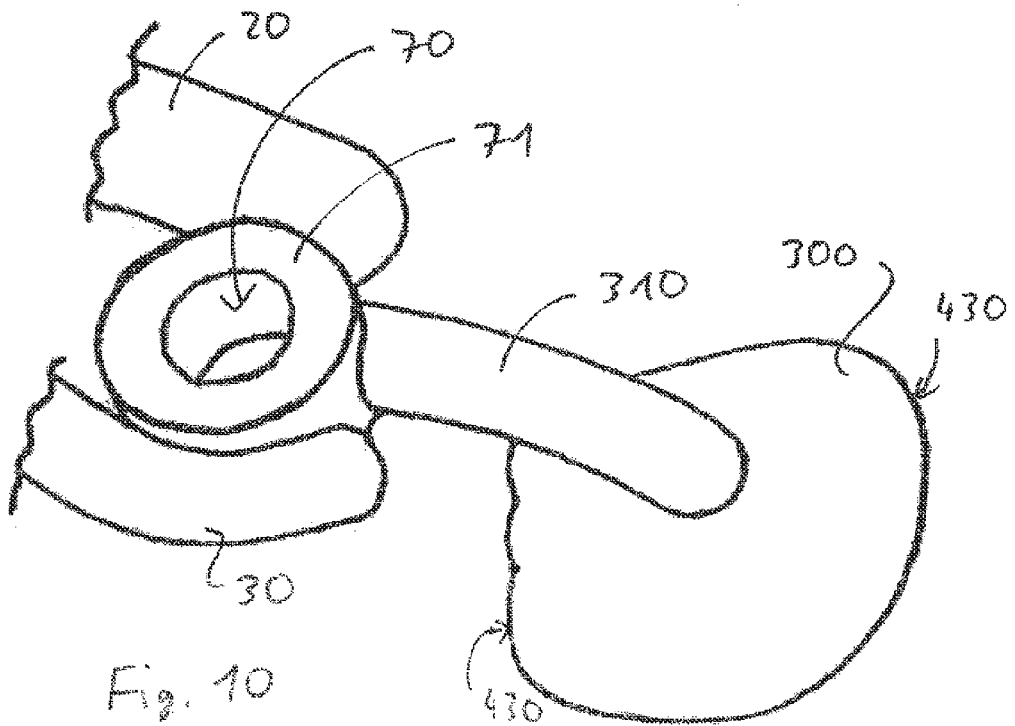

SURGICAL TEMPLATE FOR PERFORMING DENTAL IMPLANTOLOGY

TECHNICAL FIELD

The present invention relates to a surgical template for performing dental implantology, comprising at least one a drill guide bore surrounded by a guide bore ring, as well as a method for providing such a template.

PRIOR ART

From prior art a number of methods are known for manufacturing a template for providing dental implants in a jaw of a patient, especially human patients.

In dental surgery such implants are provided in a jaw to anchor dental prostheses. Such a prosthesis comprises one single false tooth or a superstructure onto which several teeth are provided.

It is always the aim of the prior art to improve the steps which have to be provided until the prosthesis can be applied to a patient. One of the important steps is drilling holes in the bone of the jaw, for which a template is to be provided.

One method and template is known from WO 2011/143725 within which a template is manufactured on the basis of a plurality of generated three-dimensional images taking into account the visible surfaces of teeth such that the template can be applied in a fitting manner via bearing surfaces or supports on these teeth presents. In this known template at least one opening is provided at the position such, that when the template has been applied in the fitting manner on teeth present in the oral cavity, the position of this opening makes it possible drilling through this opening to create a bore hole in correspondence with a selected and previously defined position.

A further template is known from US 2003/0064346, where a device to treat the teeth adjacent to a gap for the purposes of placing a dental bridge that replaces at least one missing tooth has a mounting fixture to fasten to the teeth of the patient that contains an adjustable positioning device to position the treatment tool. The positioning device in form of a sled can be moved on two parallel rails which are attached at two opposite holders of said curved mounting fixture. One of the two U-shaped sides of the holders is located at the inner lateral surface and the other is located at the outer lateral surface of its associated neighboring tooth. However, this device is only adapted to provide a guide and positioning device for one single tooth. Furthermore, the guide rails located laterally on both sides of the sled engage a common annular notch at the external perimeter of the sled in such a way that the sled and the tool head held in it can be slid on the one hand along the guide rails and on the other hand can be pivoted about the rotational axis relative to the guide rails. Therefore this positioning device is not a fixed drill guide which allows drilling one specific hole, but a lateral movement of the guide to machine the two teeth on both sides of a missing tooth.

US 2011/0217667 discloses a multifunctional diagnostic tray configured to clasp an oral structure when positioned in a mouth. The tray may be digitally designed from surface scan data of the mouth and manufactured, providing a temporary positioning reference location that may be viewed in a tomography scan data set. The tray may be used to orient and verify the tomography scan data set and the surface scan data set to create a combined master data file that may be used to determine the appropriate location for a dental implant or other dental procedure. The tooth receiving cavity of the tray is designed to contact, clasp, or otherwise engage the undercut of an oral structure, while being attached to one arc formed single rail, being positioned over the teeth. Therefore, this tray does not allow access to the teeth and cannot be used as a guide rail.

US 2011/0111362 discloses a drill guide having a support providing tooth support, soft tissue support, and/or bone support. Said drill guide comprises two superposing structures with at least two aligned holes to provide guidance for a drill bit to be engaged through these two holes.

SUMMARY OF THE INVENTION

Based on this prior it is an object of the invention to improve the bore template or jig.

One important issue relating to providing a template in one single step without the necessity to rework the template to a great extent is related to the absence of undercuts. The template according to the invention achieves this object avoiding undercuts.

A surgical template comprises at least one a drill guide bore surrounded by a guide bore ring, adapted to be positioned within the oral cavity of patient. Then according to one solution, the template comprises one complete rail and at least three first connecting points are provided that one rail. At least three second connecting points are provided in a transversal distance from said one rail through webs. In fact the second connecting points are connection portions which are attached to the webs. The first and second connecting points are adapted to be positioned on portions of the dental apparatus of the patient in his oral cavity to define the three dimensional position and orientation of the at least one drill guide bore ring. Then the rail is provided in a predetermined distance from the second connecting points providing an interspace between the rail and the connecting points allowing accommodation of the inner and outer connecting points on the rail as well as the drill guide bore ring. The template can then only comprise the number of connecting webs for connecting the one rail with the second connecting points.

A further surgical template according to the invention comprises at least one a drill guide bore surrounded by a guide bore ring and is adapted to be positioned within the oral cavity of patient. The template comprises an inner rail and an outer rail with an interspace in between. At least three inner and three outer connecting points are provided on the inner and outer rail which are adapted to be positioned on portions of the dental apparatus of the patient in his oral cavity to define the three dimensional position and orientation of the at least one drill guide bore ring. The rails are provided in a predetermined varying distance one from the other allowing accommodation of the inner and outer connecting points on the rails, wherein the template further comprises at least two connecting webs connecting the inner rail and the outer rail in a predetermined distance one from the other.

It is a preferred advantage of the invention that all outer connecting points are positioned such that there is no material of any connecting point beyond an undercut plan being the plan perpendicular to the predefined placement direction of the template onto the dental apparatus of the patient in his oral cavity. This ensures that the template cannot become stuck onto the dental apparatus.

Furthermore, it is preferred that there is at least one holder attached on the underside of the outer rail having a sufficient predefined free length to allow a clipping action in the area beyond the undercut plan onto the dental apparatus of the patient in his oral cavity to hold the template resiliently in place.

The webs connecting the rails are provided as part of a full material torus or spline body, especially a hermite spline body, attached or unitarily formed on the upper portion of the rails and preferably having a main orientational axis being in line with the main longitudinal axis of the adjacent portions of the rails.

Beside the webs connecting the rails one with another a stiffening connector can be provided between the opposite free ends of the inner rail to provide a lightweight but stiff and sturdy template.

In the case of an embodiment having only one complete rail and optionally additionally a part second rail, the complete rail is preferably the inner rail; therefore the connecting webs in this case are connecting the inner rail with the outer (second) contact points, wherein contact points mean contact point portions, since the method creates 3D model data with predetermined interfaces being represented through middle points of calculated volume spline functions.

The template can comprise an end connector provided at the free end of the rails or at a terminal guide ring. Said end connector attaches a soft tissue support having a bottom surface adapted to be complimentary to an area of soft tissue of a patient to be used as support surface.

The template can also comprise at least one drill guide bore ring which is only attached to one rail and comprises a side opening on the side opposite to said one rail, especially to the buccal side when inserted in the oral cavity of a patient. Then the side opening is larger than the diameter of a drill to be used and smaller than the diameter of a ring-like holder for the drill allowing a sidewise introduction of the drill so that this insertion requires less space in the oral cavity of the patient.

Further embodiments of the invention are laid down in the dependent claims.

A computer implemented method for producing a template according to the invention uses a computer processor and a storage means. Initially data of a three-dimensional model of the dental apparatus and the oral cavity of a patient are gathered and storing in said computer memory. The data can be provided through a e.g. X-ray or CT-scan or by transforming photographs. Based on this data the position and orientation of at least one guide bore ring is defined in the three-dimensional model data and stored. Then positions and orientations of at least six connecting points on the model of the dental apparatus are calculated, providing a well-defined positioned system for the bore ring, when the six points are interconnected and connected with the bore ring. The inner connection points are then interconnected with a curved inner rail as three-dimensional model data connecting an inner orientation and attachment portion of the guide bore ring with said at least three inner connecting points. The same procedure is applied for providing a curved outer rail as three-dimensional model data connecting an outer orientation and attachment portion of the guide bore ring with at least three outer connecting points and both sets of data are stored in the computer memory. Finally at least one web connecting the inner rail with the outer rail is defined, which is at a spaced locations from the bore ring connection portions. Then, based on this data, they are transformed into signal and control data for a production machine, as e.g. a rapid-prototyping apparatus or a milling apparatus, allowing for a quick production of an improved template.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 6 shows a schematic cross-sectional side view on the template according to FIG. 5, explaining the advantages of the open access side;

FIG. 7 shows a schematic cross-sectional side view on a template according to a further embodiment using an additional sleeve;

FIG. 8 shows a schematic cross-sectional side view on a template according to a further embodiment only using a holder;

FIG. 9 shows a schematic side view on a template according to a further embodiment having a soft tissue support and/or bone support; and FIG. 10 shows a schematic view from above on a template according to a further embodiment having a soft tissue support which is directly attached to a drill guide ring.

DESCRIPTION OF PREFERRED EMBODIMENTS

Figure 1:
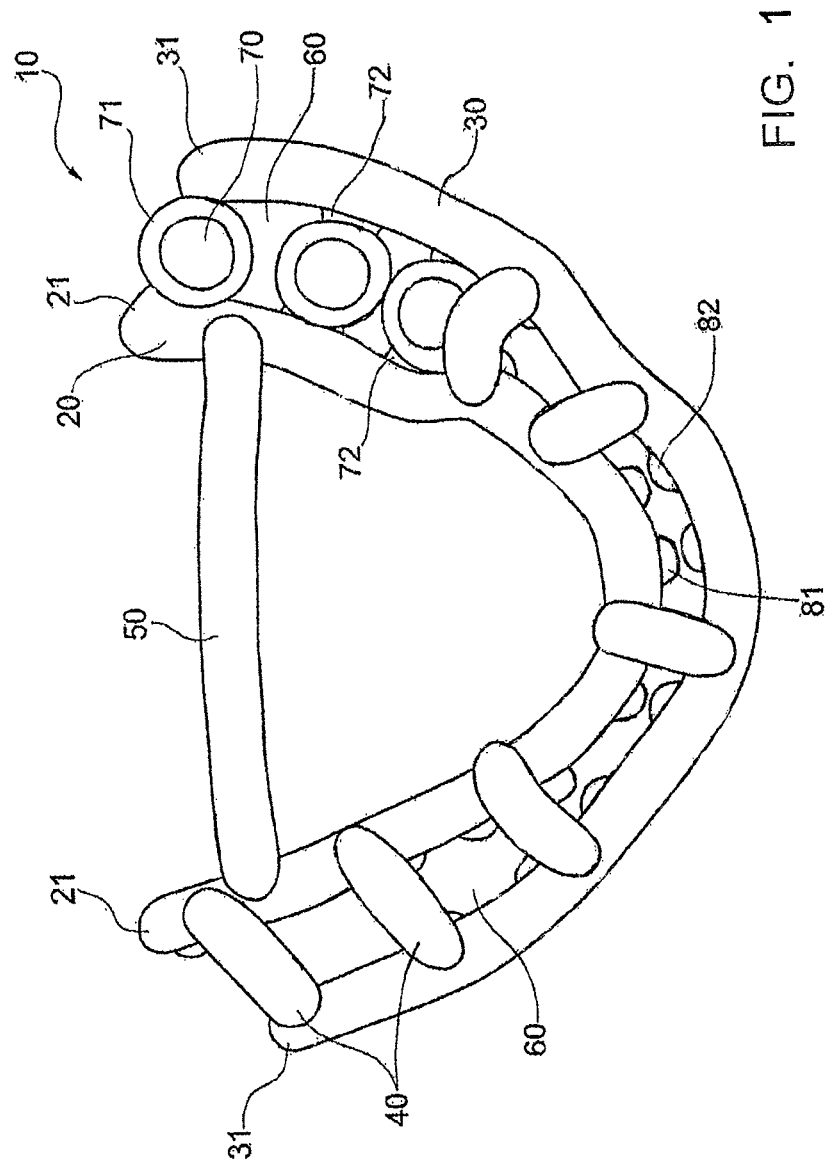
FIG. 1 shows a schematic view from above on a template for a lower jaw according to an embodiment of the invention.

FIG. 1 shows a schematic view from above on a template 10 for a lower jaw according to an embodiment of the invention. Within this embodiment template 10 comprises a complete inner rail 20 and a complete outer rail 30. These rails 20 and 30 are in the embodiment shown made of a plastic material, especially through rapid-prototyping, and the rails 20 or 30 comprise in a cross-section an essentially regular and constant diameter which is based on a cylindrical curved rod. The rails 20 and 30 are preferably made of solid material having such a circular cross-section but they might be made at least partially hollow and the outer circumference in a cross-section can also be e.g. elliptical. In fact, the rails 20 and 30 appear as full-material tubes. Beside rapid prototyping for transferring 3D model data into the geometry of the template 10 it is also possible to use machining procedures as milling, based on a plastics material or another different basic material. The template 10 can be produced on the basis of different materials which could be certified for the temporary use within the oral cavity of a patient and are at the same time limited to materials which can be used for the production of the template. It is also possible to provide the template 10 in metal or metal-containing compounds.

The cross-sections of the rails 20 and 30 can be equal or the outer rail 30 can be thicker or thinner than the inner rail 20. Preferably, the circumferential surface of the rails 20 and 30 is always rounded. Between rails 20 and 30 are provided a number of, in the present embodiment six, webs 40 providing a unitary template 10. At least one web 40 is necessary in addition to the connection between the rails 20 and 30 via the bore ring attachments 72. The length of the rails 20 and 30 is sufficient to cover the positions of at least eight teeth of a human being and covers preferably most of the arc of teeth of a human being, i.e. it covers twelve to sixteen teeth. The inner and the outer rails 20 and 30, where applicable run inside and outside, respectively, of the arc of the teeth structure of the patient. The webs 40 run essentially perpendicular to this arc, i.e. they run essentially parallel to side surfaces of the teeth or cross the gaps of missing teeth.

Furthermore it is preferred that one or more connectors 50 are provided between the free ends 21 of the inner rail 20; but if there is no interfering web 40, they can also be provided between the free ends 31 of the external rail 30. The connector 50 is provided to enhance stiffness of the template 10. Webs 40 and connector 50 have preferably a constant diameter which can be e.g. one third to two thirds of the diameter of the rails 20 and 30. The connector 50 can be provided outside of the drawing plan of FIG. 1 wherein it is preferred that the inner portion of the connector 50 is directed to the palate. It also possible to predetermine a varying diameter of the connector 50 over his length as well as for the webs 40 or the rails 20, 30.

Webs 40 are always provided on the upper side of the two rails 20 and 30, respectively, and are directed away from the jaw for which the template 10 is intended, i.e. the curvature of the webs 40 is directed to the opposite jaw; if the template 10 shown from above is intended to be used with the lower jaw than the webs 40 are curved in direction of the upper jaw, when the template 10 is put into the oral cavity of a patient. As can be seen from FIGS. 2 and 3 the webs 40 mainly cover half of a circle and the webs 40 are formed by a so called torus. The torus 40 is attached or unitarily formed on the upper portion of each of the rails 20, 30 and preferably having a main axis 104 being in line and essentially parallel with the main axis 102, 103 of the adjacent portions of the rails 20 as well as 30. The bridges or webs 40 can also be chosen different and can be predetermined following a spline, e.g. a hermite spline, determining the form of the connecting web through defining the two intended middle attachment points of the web 40 on the surface of the rails 20 and 30, respectively, as well as the tangent, allowing for a specified unique torus path between the two mentioned points.

The diameter of the rails 20 and 30 is preferably chosen in a way that they provide enough stability together with the consequential free space 60 between them to allow a better visibility of the oral cavity of a patient and to allow direct access.

FIG. 1 furthermore shows three areas 70 as drill guide bores each comprising a ring portion 71 as drill guide ring, which rings 71 are connected by an orientation portion 72 to the inner rail 20 as well to the outer rail 30, respectively. These rings 71 with the through going hole 70 are oriented in a predefined way to provide the bore template based on the predefined data to calculate the direction of the drilling into the bone of the jaw of a patient. The rings 71 can accept an e.g. metallic drill guide sleeve 420, which is introduced into the ring 71 by e.g. clamping or it is e.g. bonded through an adhesive layer 421 inside the ring 71. The use of such a sleeve 420 is explained in connection with FIG. 7. The use of such a template or a similar jig without using such a sleeve 420 is shown in FIG. 8.

It is noted that the orientation of the rings 71 is not such that their axis is perpendicular to the drawing plan or to the main longitudinal direction of the rails 20 and 30. Their orientation is chosen to allow the correct orientation of the bore to be drilled for the implant through the drill guide sleeve. The rings 71 are fixed to the rails 20, 30 and cannot be moved.

Especially in this region of the template 10, the free space 60 provides an improvement for the drilling and it can be seen that the rails 20 and 30 of the template 10 have more distance one from the other in this region which is easily achieved by the snake or sausage like form of the round rails 20 and 30, respectively. A person using the rings 71 for drilling has a clear view of the dental apparatus in the oral cavity at that place. It is an advantage of the template 10, that the drilling area in the oral cavity can be directly visually inspected during the intervention, since beside the rings 71 there are additional free areas 60 between the rails 20 and 30 and the bore rings 71 and possible webs 40 to provide cooling during drilling.

Furthermore, several outer contact points 82 and inner contact points 81 can be distinguished between the two rails 20 and 30. There positioning and function will be explained in connection with FIGS. 2 and 3. These contact points 81 and 82 are provided during the construction of the template 10. These contact points 81 and 82 are protrusions at the two rails 20 and 30 and are mainly oriented perpendicular to the respective rail 20 or 30 and they have a small length compared to the rails 20, 30. They are provided individually on each rail 20 and 30 and they are not directly connected one to another, i.e. one contact point 81 is "connected" to its corresponding contact point 82 for the same tooth only via one or more webs 40.

Furthermore said contact points 81 or 82 can visually be very easily inspected to see if any misplacement of the template 10 is visible or a gliding of the template 10 would occur. Additionally, any possibly problematic contact points 81 or 82 can be identified and adapted locally through the technician. In this context it is a further advantage that the technician has a clear view of the difference between the limited area of the contact points 81 or 82 and the supporting rail body 20 or 30. It is a further advantage that contact points 81 and 82 are connected with stiff portions of rails 20 and 30 and a web 40, but that this has not to be in a straight line. It is especially possible and preferred to choose the contact points 81 and 82 (and connector 300) based on the existing teeth, bone structure or soft tissue elements, but that they can be freely chosen and are not restricted to one single element as in the prior art. It is also possible to use the 3D modeling with its snake-like structure following a spline based calculation to provide enough space to model the contact points on the rails 20 and 30, instead of being forced to model imperfect contact points on a specific predetermined arc-like rail as in the prior art.

The advantage of the geometry of the template 10 is that it does not have any undercuts as well be se seen in the following description. This has the advantage during use that the template 10 cannot jam or become stuck while placed, even if the teeth which are used for placing the template 10 are very oblique.

Figure 2:
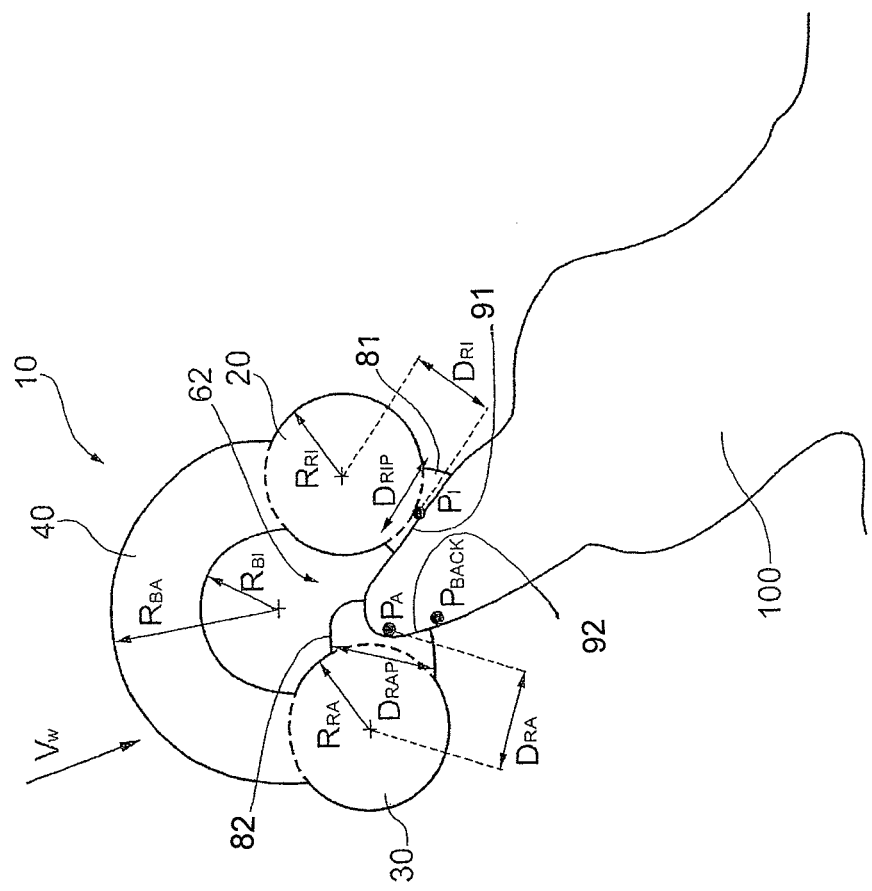
FIG. 2 shows a sketch of a section through a front tooth and the template according to FIG. 1.

FIG. 2 shows a schematical side view and geometrical cross section through a tooth 100 of a patient together with the template 10 according to FIG. 1 which is placed with two contacting points 81 and 82 on said tooth 100. Furthermore one single connecting web 40 can be distinguished between the inner rail 20 and the outer rail 30.

The diameter of the connecting web 40 within the embodiment shown in the drawings is approximately two third of the diameter of the identical diameters of rail 20 and 30. Web 40 is connecting the rail 20 and 30 in an essential radial way, with a short connection perpendicular to the main direction of the rails 20 and 30 in this region. Of course, depending on the choice of materials the diameter of webs and rails can be adapted. In any case, the elements of the template according to the invention comprise a framework with struts and no extended full surfaces, neither for or near the fixating contact points 81, 82, nor for the connection between the different contact points 81, 82 and the bore ring 71. This is achieved with a framework of thin struts allowing for an interspace 60 at all instances, near the fixation points as well as near the working and drilling area, provided by a two rail proposal.

Furthermore, each web 40 of the embodiment as shown usually covers half of a torus between the rails 20 and 30. The outer connecting point 82 is provided in the interspace between the two rails 20 and 30 still leaving a free space 62 at that place. The second inner connecting point 81 is unitarily formed with the inner rail 20 and comprises a complementary contact surface 91 for a positioning of the point 81 on the inner portion of the tooth 100. The point 82 is placed on the upper portion of the tooth and has rounded contact surface 92.

It is possible that the attachment points 81 and 82 are not extensions being entirely made of additional material over the rail material 20 and 30 but would be "inside" the diameter of the rails 20 and 30 within a predefined recess. This might especially be true in a situation as for locating point 82, where the outermost point (from the anatomical point of view) $P_A$ is near the broken line of the outer rail diameter 30. However, in such a case it is preferred as shown in FIG. 1 to provide additional curvatures of the snake like rails 20 and 30 allowing for improved stability through uniform thickness of the rails 20 and 30.

The arrow with the denomination $V_W$ is the working direction or placement direction to clip the template 10 onto the tooth 100 of the patient. This direction is similar for different cross-sections of the template 10. Point $P_A$ is now the medium outer contact point of locating portion 82 with the tooth 100. $P_I$ is the inner point on the tooth 100 connecting with the surface locating portion 81.

The point $P_{Back}$ is the point marking the begin of the undercut area related to $V_W$ as working direction, in other words, any material of the template 10 which would be placed on the tooth 100 beyond and lower of $P_{Back}$ in the direction of said arrow would be placed in the undercut area which may provide a clamping action.

$R_{RI}$ is the radius of the inner rail 20; $R_{RA}$ is the radius of the outer rail 30; parameters of the torus can be defined through $R_{BI}$ as inner radius as well as $R_{BA}$ as outer radius of the bridge or web 40. $D_{RA}$ is the distance between the rail 30 and the tooth 100 wherein $D_{RI}$ is the distance between the inner rail 20 and the tooth 100. The stability of the contact 91 can be defined by $D_{RIP}$ for the diameter at the inner rail 20 at contact point 81 wherein $D_{RAP}$ is the diameter of the outer rail 30 at the contact point 82.

The template 10 is placed on the teeth 100 through the predefined point contacts $P_A$ and $P_I$ which is an advantage over prior art wherein an area contact surface is usually provided.

The contact points 81 and 82 can be chosen above the undercut line which is defined by the working direction. In other words $P_A$ should be closer to the web portions 40 then $P_{Back}$.

The distances $D_{RIP}$ or $D_{RAP}$ of the rails 20 and 30 at the tooth 100 can be predefined through the corresponding distance of the rail 20 and 30 leaving more or less space 62 between them. The web portion 40 is then to be adapted and can be provided with a more oval form.

The template 10 comprises at least three inner contact points 81 and three outer contact points 82 wherein the number, form and position of these points 81 and 82 are based on the actual situation in the oral cavity of the patient.

Within the construction method, the rails 20 and 30 are defined based on the contact point distance providing the snake or sausage like curvature of the rail. In the method of the construction of the template 10 it is only important at that point in time that the webs 40 and connection portions 50 are chosen.

Figure 3:
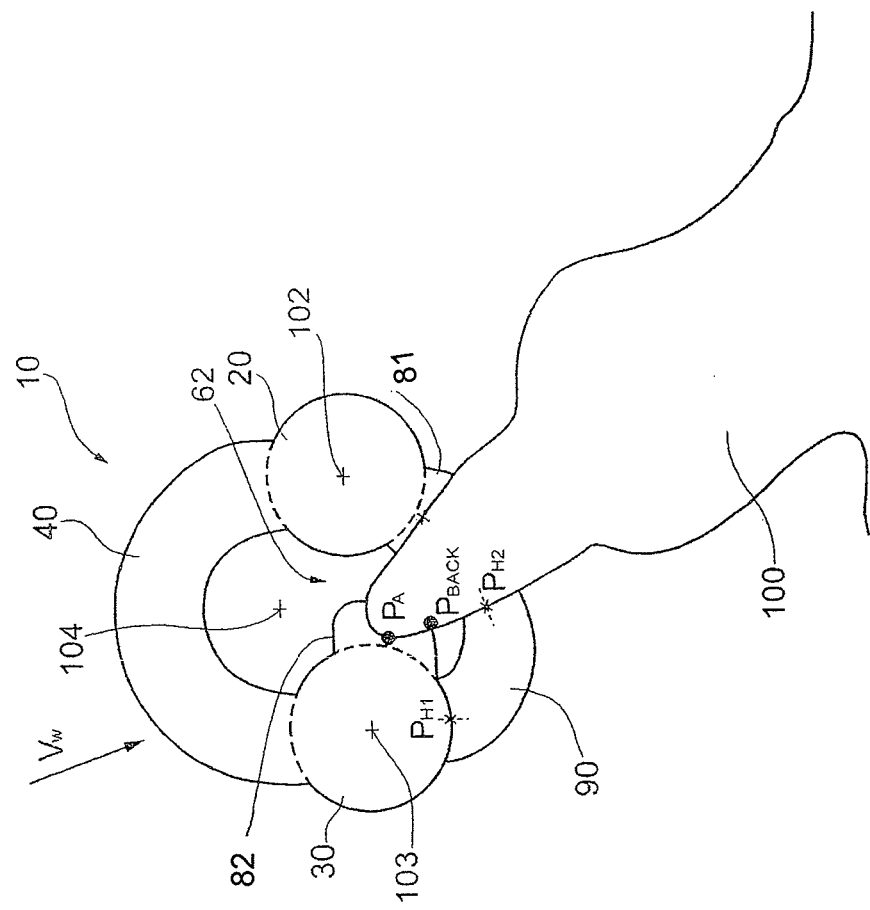
FIG. 3 shows the situation of the template according to FIG. 2 together with a holder to lock the template on the tooth.

FIG. 3 shows an advantage of providing a specific holder 90 at specific places of the outer rail 30 connecting the outer rail 30 with a specific median point $P_{H2}$ which is on the opposite side of $P_{Back}$, in view of $P_A$ in connection with the working direction $V_W$ to provide a fixation element according to FIG. 2. This fixation element 90 avoids that the surgeon has to maintain the template 10 against the teeth 100. Said point $P_H$ is then exceptionally chosen within the undercut area under tooth 100. Then a resilient spline is provided between the points $P_{H1}$ and $P_{H2}$ as a partial torus which might have a changing geometry. In the embodiment shown in FIG. 3 the holder 90 has a a smaller diameter on the tooth contacting surface than when having an unitary connection with the outer rail 30. The material of the holder 90 can be identical to the material of the rails 30 or it can be more resilient.

Initially, the contact points 82 of the outer rail 30 are calculated and later-on the chain of inner contact points 81 is defined. Usually, it is sufficient to provide one or two single holder 90 having this snapping effect in order to avoid an otherwise not preferred clamping action on other teeth 100. The holder 90 can be provided in connection with a pair of corresponding inner and outer connection points 81 and 82 or it can be provided in the longitudinal direction of the rails 20 and 30 in the middle between two pairs of connection points 81 and 82 on e.g. different teeth beside the tooth 100 of the holder, so that at the position of the holder, there is only the holder 90 pushing from an undercut position on the outside of a tooth 100 between two adjacent pairs of locating points 81 and 82. If two holder 90 are provided they are preferably provided on diametrically opposite portions of the template 10, i.e. more adjacent to the opposite free ends 31 of the outer rail 30 then to the middle of the template.

Figure 4:
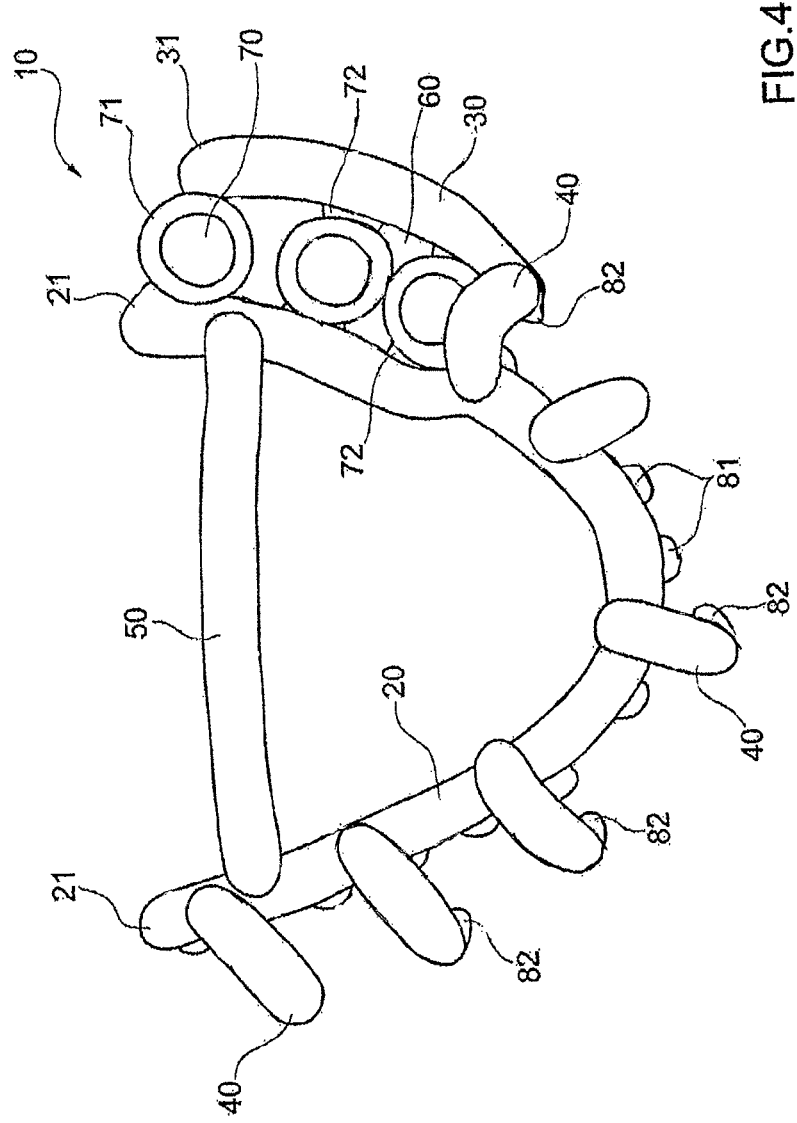
FIG. 4 shows a schematic view from above on a template for a lower jaw according to a further embodiment of the invention.

FIG. 4 shows a schematic view from above on a template 15 for a lower jaw according to a further embodiment of the invention. Within this embodiment only one full rail, the inner rail 20 is provided. Similar features within all embodiments receive identical reference numerals. The outer rail 30 is provided only in the vicinity of the drill guide ring 71, but it is also possible that the drill guide ring 71 is held by only one orientation portion 72 attached to the inner rail 20; especially if the rail 20 and the orientation portion 72 and possible the drill guide ring 71 are provided in metal.

In FIG. 4 the webs 40 have an additional function beyond connecting the rails 20 and 30, where applicable. The contact points 82 on the outer side of the tooth 100 are extensions of the webs 40; or in other words: following of generating the form and position of the contact points 82 beside contact points 81, the inner contact points 81 are connected by the curved inner rail 20, whereas for the outer contact points 82 the webs 40 are generated to provide the connection to the inner rail 20 instead. Therefore the spline function is here not generated to connect the two rails 20 and 30 but the inner rail 20 with a specifically created contact point portion 82. In FIG. 4 five such contact points 82 are attached via webs and one contact point 82 is attached at the end of the reduced outer rail 30.

In a further embodiment not shown in the drawings, the template is created based on an outer rail 30 and the webs 40 connect that outer rail 30 with inner contact points 81 and provide attachment points for the connector 50.

Figure 5:
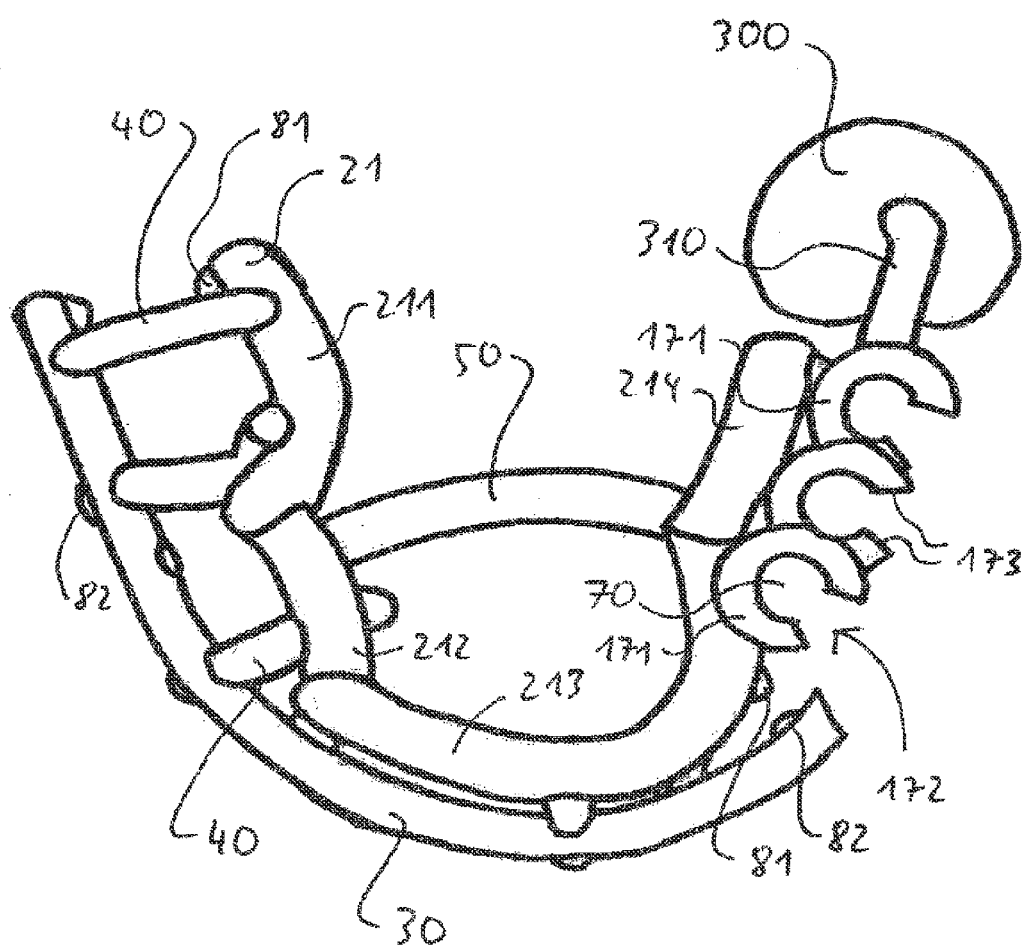
FIG. 5 shows a schematic view from above on a template for a lower jaw according to another embodiment of the invention with an open access side.

FIG. 5 shows a schematic view from above on a template for a lower jaw according to another embodiment of the invention with an open access side 172 for rings 171 and additional with a soft tissue support connector 300. Although these features of connector 300 and open rings 171 are shown here in one embodiment, it is possible to use the open rings 171 together with a one ring structure as in FIG. 4 and on the other hand, it is possible to use the soft tissue support connector 300 together with closed rings 71 as shown in FIG. 1pp. Similar features have received similar reference numerals. It is noted that the soft tissue connector 300 can also be a hard tissue connector in the sense of a bone material connector as will be explained below in connection with FIG. 9.

Within the embodiment of FIG. 5, the inner ring 20 is segmented in three separately curved but joined portions 211, 212, 213 and 214 forming the inner ring 20. The outer ring 30 ends after between ⅔ and ¾ of the usual circumference of a human oral structure to avoid coverage of the three rings 171. The connecting contact points 81 and 82 are provided as usual on the rails 20 and 30. The same is true for the connector 50 between the inner ring portions 212 and 214.

Each of these rings 171 is only attached/molded together with the inner ring 20 and the neighbor rings 171, if applicable. The outermost ring 171 is attached with a soft support web 310, e.g. a curved cylindrical connector with a plate like but curved soft tissue support 300, which will be explained in connection with FIGS. 9 and 10.

The open rings 171 have an inner through bore 70 as within the embodiment of FIG. 1, but also have an open access side 172, here directed to the outer side. Therefore two side surfaces 173 appear creating a canal through which a drill 402 can be advanced as will be explained in connection with FIG. 6.

FIG. 6 shows a schematic cross-sectional side view on the template according to FIG. 5, explaining the advantages of the open access side 172. Only open ring 171 is shown in FIG. 6, positioned above the oral structure surface, but without representation of further teeth. A drill 402' is schematically shown in a holder 400', both in an initial position beside the template. Therefore, the drill 402' is shown beside the ring end surface 173 and the holder 400' is positioned above the ring 171. Therefore the height which has to exist within the mouth of a patient is reduced to the value of length 401 above the template, since the drill bit itself is already positioned in a short distance above the structure surface 200 and therefore not above but along the rail structure 20, 30. Then the holder 400' with the drill 402' is moved in a transverse movement 403 through the open side 172 and between the side surfaces 173 into the through bore 70. Since the drill 402 has a smaller diameter then the open space provided between the surfaces 173, it can be positioned inside the bore 70. Then the drill 402 is maintained in this position and the holder 400 is moved downwards and towards the surface 200 in the open slit or free ring space 410 according to the arrow 405. The subsequent movement of drill 402'/402 along the line 403 and the holder 400'/400 along line 405 allows the user of the device to enter the drill 400 from above into the hole 70, but to enter it sideways and to maintain it in the hole through the holder 400 having an outer diameter being larger than the distance between the side surfaces 173. These surfaces are shown as radially oriented surfaces, they can also provide a slit of constant width in other embodiments or it may be provided as a funnel like opening wherein the side surfaces are reducing the width of the opening until the semi-cylindrical opening for the fitting reception of the drill 402 or holder 400. But also in this case the diameter of the hole is not larger than, i.e. is about the same size as, the holder 400, so that only the opening side 172 is missing from the open ring 171.

It is also possible, but not preferred, that the side opening 172 on the side opposite to said one rail 20 is larger than the diameter of the ring-like holder 400 for the drill 402, so that the drill 402 together with its holder 400 can engage the hole 70 from the open side. However, in such a case, the dentist has to manually hold the position of the holder 400 and drill 402 in the opening 70, but this is then supported in the longitudinal direction by the cylindrical wall as well as for an arc of approximately 230 to 270 degrees in the circumference direction of the hole 70 which then can open into funnel like side walls 173.

FIG. 7 shows a schematic cross-sectional side view on a template according to a further embodiment using an additional sleeve 420. The hole or through-bore 70 is conventionally used to receive a sleeve 420, especially a metal sleeve, if the template is made out of plastics material. The sleeve 420 is usually pushed into the hole 70 of the ring 71 and glued through use of an adhesive layer 421 as shown in the magnified portion. Usually the sleeve 420 has an upper flange to stop the introduction movement at the upper surface of the ring 71. However, then we have two fittings between the ring 71 and the sleeve 420 on one hand and between sleeve 420 and holder 400 of the drill 402 on the other hand. Therefore it is preferred to only use the holder 400 as shown in FIG. 8, being a schematic cross-sectional side view on a template according to a further embodiment only using a holder 400. Holder 400 as well as drill 402 are shown schematically, having a L-shape. The shape depends on the drilling system used within the surgical kit as provided by different manufacturers. Usually the upper horizontal portion of the drill 40 is the drilling machine whereas the perpendicular portion comprises the drill bit. The system according to FIG. 7 uses one fitting more than the proposal according to FIG. 8, when the drill 402 is guided through the spoon like holder 400. The omission of sleeve 420 is especially valuable in connection with the side open rings 171, which provide the access slit between the surfaces 173 from the buccal side. The drill 402 is inserted extraoral within the holder 400 and then the two movements 403 and 405 are executed subsequently within the oral cavity of a patient.

FIG. 9 shows a schematic side view on a template according to a further embodiment having a soft tissue support 300 and/or bone support; and FIG. 10 shows a schematic view from above on a template according to a further embodiment having a soft tissue (or bone) support 300 which is directly attached to the end drill guide ring 71. Drill guide ring 71 is the last ring 71 between the rails 20 and 30 and is connected with a support web 310 to the soft tissue support 300. The support web 310 is of similar thickness as are rails 20 and 30 and preferably connect the soft tissue support 300 in the middle. The soft tissue support 300 as shown in FIG. 9 is in direct 3D-connection with the surface 301 of the tissues or the bone portion of a patient. This allows an alternative solution in cases where the patient has only a limited number of usable teeth for the contact points 81 and 82 or if the distances are such that the stiffness of the template needs preferably a support point as the support 300 on the other side of the rails 20 and 30. Then this support 300 can be positioned on the mucosa 200 of a patient, providing a specified circumference 430 of the support, wherein the portion 301 inside the circumference is scanned within the surface data of the patient and restituted via a negative mold. Then this support portion can be used as a remaining tooth within the layout of the template according to the invention.

An area of soft tissue for the connector plate 300 can be any area within the oral structure of a patient as e.g. gum which can be used as supplementary contact point or support point, especially in the case, when the existing tooth structure does not provide enough support points 81/82. Of course, if the soft tissue is removed from the underlying bone structure, e.g. during the surgical intervention, such areas can also be bone areas. The image of FIG. 9 can be provided by the scan. This is also true, if the dentist opens the soft tissue area and applies the support 300 directly on the underlying bone material. There are other ways to provide this surface as taking a negative cast to provide a plaster model which is then scanned or the scan can be provided in an intraoral picture. In case of a support 300 on the bone material, applied after removal/opening of the covering soft tissues in the invention, the surface data can be provided from a previous radio scan, e.g. the 3D CT/DVT-scan of the patient. Then the template can be provided as a combination base on the intraoral image by visible light sources (for existing teeth and soft tissues) and on the radio image (for existing teeth as a second source or for the superposition of the image results and the jawbone material).

LIST OF REFERENCE SIGNS

| | |
|---|---|
| 10 | template |
| 15 | template |
| 20 | inner rail |
| 21 | free end of inner rail |
| 30 | outer rail |
| 31 | free end of outer rail |
| 40 | web |
| 50 | connector |
| 60 | free space |
| 62 | free space |
| 70 | drill guide bore |
| 71 | drill guide ring |
| 72 | orientation portion |
| 81 | contact point on the inner side |
| 82 | contact point on the outer side |
| 90 | holder |
| 91 | contact surface |
| 92 | contact surface |
| 100 | tooth |
| 102 | axis of inner rail at any cross-section |
| 103 | axis of outer rail at any cross-section |
| 104 | axis of a web |
| 171 | open drill guide ring |
| 172 | side opening |
| 173 | ring end surfaces |
| 200 | oral structure surface |
| 211 | rail portion |
| 212 | rail portion |
| 213 | rail portion |
| 214 | rail portion |
| 300 | soft tissue support |
| 301 | 3D soft tissue surface |
| 310 | soft support web |
| 400 | holder |
| 400' | holder (initial position) |
| 401 | free height |
| 402 | drill |
| 402' | drill (initial position) |
| 403 | lateral movement of the drill |
| 405 | advance movement of the holder |
| 410 | free ring space |
| 420 | sleeve |
| 421 | adhesive |
| 430 | circumference |

The invention claimed is:

1. A surgical template, adapted to be positioned on portions of a detention of a patient within an oral cavity of the patient, comprising:
   a first and a second rail, one rail being an inner rail and one rail being an outer rail,
   at least one drill guide bore ring positioned between the inner and outer rails and having a drill guide bore,
   at least three spaced apart first contact points protruding from the inner rail and being formed in a one-piece relationship with the inner rail,
   at least three spaced apart second contact points protruding from the outer rail and being formed in a one-piece relationship with the outer rail, and
   at least two connecting webs connecting the inner rail and the outer rail in a predetermined distance one from the other,
   wherein the first and second contact points are adapted to be positioned and clipped on portions of the dentition of the patient to define the three dimensional position and orientation of the at least one drill guide bore ring,
   wherein the rails are provided in a predetermined distance, one from the other, providing an interspace between the rails and the first and second contact points, thereby allowing accommodation of the first and second contact points on the rails and accommodation of the drill guide bore ring.

2. The surgical template according to claim 1, comprising a portion of a second rail provided in the vicinity of the drill guide bore rings, wherein bore ring connectors are attached to the inner and outer rail portions allowing holding the drill guide bore rings with a frame extending on opposite sides of the dentition.

3. The surgical template according to claim 1, wherein the rails are provided in a predetermined varying distance one from the other providing the interspace between the rails allowing accommodation of the first and second contact points on the rails as well as the drill guide bore ring.

4. The surgical template according to claim 1, wherein the rails are free-form curved cylinders.

5. The surgical template according to claim 4, wherein the free-form rails are provided as part of a full material torus or spline body or hermite spline body.

6. The surgical template according to claim 1, wherein the webs connecting the rails are provided as part of a full material torus or spline body or hermite spline body, attached or unitarily formed on the upper portion of the rails.

7. The surgical template according to claim 6, wherein the webs having a main orientational axis being in line with the main longitudinal axis of the adjacent portions of the rails.

8. The surgical template according to claim 7, wherein each web has a main axis being in line and essentially parallel with the main axis of the adjacent connected portions of the rails.

9. The surgical template according to claim 1, wherein all outer contact points are positioned such that there is no material of any outer contact point beyond an undercut plan being the plan perpendicular to the predefined placement direction ($V_W$) of the template onto the dentition of the patient in his oral cavity.

10. The surgical template according to claim 9, wherein at least one holder is provided attached on the underside of the outer rail or on the underside of a contact point connecting web in the case of one complete rail having a sufficient predefined free length to allow a clipping action in the area beyond the undercut plan onto the dentition of the patient in his oral cavity to hold the template resiliently in place.

11. The surgical template according to claim 1, wherein a stiffening connector is provided between the opposite free ends of the inner rail.

12. The surgical template according to claim 1, wherein at least one of the at least two webs is formed by the bore ring together with the bore ring connectors attaching said bore ring to the two opposite rails.

13. The surgical template according to claim 1, wherein an end connector is provided at the free ends of the rails or at a terminal guide ring attaching a soft tissue or bone support having an bottom surface adapted to be complimentary to an area of soft tissue of a patient to be used as support surface.

14. The surgical template according to claim 1, wherein at least one drill guide bore ring is only attached to one rail and comprises a side opening on the side opposite to said one rail, wherein the side opening is larger than the diameter of a drill to be used and smaller than the diameter of a ring-like holder for the drill.

15. A surgical template, adapted to be positioned on portions of a dentition of a patient within an oral cavity of the patient, comprising:
one rail,
at least one drill guide bore ring having a drill guide bore,
at least three spaced apart first contact points being formed in a one-piece relationship with the one rail,
at least three spaced apart second contact points being provided as protrusions in a transversal distance from said one rail,
at least two connecting webs connecting the one rail with the second contact points in a predetermined distance one from the other,
wherein the first and second contact points are adapted to be positioned and clipped on portions of the dentition of the patient to define the three dimensional position and orientation of the at least one drill guide bore ring,
wherein the rail is provided in a predetermined distance from the second contact points providing an interspace between the rail and the second contact points allowing accommodation of the first and second contact points on the rails and accommodation of the drill guide bore ring.

16. The surgical template according to claim 15, wherein the webs connecting the one rail with the second contact points are provided as part of a full material torus or hermite spline body, attached or unitarily formed on the upper portion of the second contact points.

17. The surgical template according to claim 15, wherein said contact points comprise inner and outer contact points and all outer contact points are positioned such that there is no material of any outer contact point beyond an undercut plan being a plan perpendicular to a predefined placement direction ($V_W$) of the template onto the dentition of the patient in the oral cavity.

18. The surgical template according to claim 17, wherein at least one holder is provided attached on an underside of a contact point connecting web and having a sufficient predefined free length to allow a clipping action in an area beyond the undercut plan onto the dentition of the patient in the oral cavity to hold the template resiliently in place.

19. The surgical template according to claim 15, wherein at least one drill guide bore ring is attached to the rail and comprises a side opening on the side opposite to said one rail, wherein the side opening is larger than the diameter of a drill to be used and smaller than the diameter of a ring-like holder for the drill.

20. A method for producing a template, comprising the steps of:
providing a computer having a processor and a computer memory and being programmed to execute the steps,
gathering data of a three-dimensional model of a dentition and an oral cavity of a patient,
storing said data of the three-dimensional model in the computer memory,
defining position and orientation of at least one drill guide bore ring in the three-dimensional model data,
storing said data of the position and orientation of said at least one drill guide bore ring in the computer memory, said drill guide bore ring having a drill guide bore,
defining positions and orientations of at least three first inner and three second outer contact points on the model of the dentition providing a well-defined positioned system when said at least three first inner contact points, said at least three outer contact points and said at least one drill guide bore ring are connected,
storing said data of the positions and orientations of the contact points in the computer memory;
providing a curved first rail as three-dimensional model data connecting a first orientation and attachment portion of the guide bore ring with at least three first contact points, storing said data of the curved first rail in the computer memory;
providing either (1) a curved second rail as three-dimensional model data connecting a second orientation and attachment portion of the drill guide bore ring with at least three second contact points and storing said data in the computer memory or (2) contact point connecting webs as three-dimensional model data connecting the at least three second contact points with the first rail and storing said data in the computer memory; and
in the case that there are first and second rails, providing at least one web as three-dimensional model data connecting the first rail with the second rail and storing said data in a computer memory;
transforming the stored data into signal data for a production machine, as a rapid-prototyping apparatus or a milling apparatus.

21. The method according to claim 20, wherein the method comprises after creation of the first rail data, providing a curved second part rail as three-dimensional model data attaching with one or more second orientation and attachment portion of the guide bore ring and storing said data in a computer memory and providing one or more webs as three-dimensional model data connecting the curved second part rail with the first rail and storing said data in a computer memory.

* * * * *